United States Patent [19]

Schaeffer et al.

[11] 4,110,079

[45] Aug. 29, 1978

[54] ANALYTICAL ELEMENT FOR CLINICAL ANALYSIS

[75] Inventors: James R. Schaeffer, Penfield; Louis M. Minsk, Rochester; Richard E. Stevens, Penfield, all of N.Y.

[73] Assignee: Eastman Kodak Company, Rochester, N.Y.

[21] Appl. No.: 805,215

[22] Filed: Jun. 9, 1977

[51] Int. Cl.$^2$ ............................................. G01N 31/22
[52] U.S. Cl. ................................................. 23/253 TP
[58] Field of Search ............ 23/253 TP; 116/114 AM

[56] References Cited

U.S. PATENT DOCUMENTS

2,543,181  2/1951  Land ........................................... 95/8
3,697,227  10/1972  Goldstein et al. ................. 23/253 TP
3,992,158  11/1976  Przybylowicz et al. ........ 23/253 TP Primary Examiner—Robert M. Reese
Attorney, Agent, or Firm—Ronald P. Hilst

[57] ABSTRACT

An analytical element for use in the clinical assay of an analyte contained in a biological liquid sample which is applied from an external source to a substantially planar sample receiving suface of the element. The analytical element comprises a porous layer bearing the aforementioned sample receiving surface; at least one dry reagent material for use in the assay; and one or more associated rupturable pod-like member(s) containing a liquid reagent for the assay, such liquid reagent, upon rupture of the pod-like member(s), being released into the element.

10 Claims, 6 Drawing Figures

ANALYTICAL ELEMENT FOR CLINICAL ANALYSIS

BACKGROUND OF THE INVENTION

Cross-Reference to Related Application

Reference is made to Figueras, U.S. Patent Application Ser. No. 759,527, filed Jan. 14, 1977, entitled "Element For Analysis of Liquids". Certain of the multilayer analytical elements disclosed in the aforementioned Figueras application (such as that illustrated in FIG. 5 of the Figueras application) represent specific embodiments of the present invention.

FIELD OF THE INVENTION

The present invention relates to an analytical element for the clinical analysis of biological liquids.

BACKGROUND OF THE INVENTION

Clinical analysis of biological liquids from human or other mammalian sources, especially aqueous liquids such as blood, serum, urine, and similar biological liquids is often desirable or necessary. Various elements to facilitate such analyses or assays are known. Such elements have often included a reagent for a chemical substance under analysis, termed analyte herein, which reagent, upon contacting a biological liquid sample containing the analyte, produces formation or destruction of a colored or other type of detectable material in response to the presence of the analyte. Much recent development work has attempted to provide elements useful in diagnostic or clinical analysis, where testing of biological liquids must produce a highly quantitative result, rapidly and conveniently.

In an attempt to satisfy the needs of clinical analysis work for rapid, quantitative results, a variety of solution chemical techniques, sometimes referred to in the art as "wet chemistries", have been developed for the clinical laboratory environment and have been particularly adapted for automated clinical analysis work. In such "wet chemistries" clinical reagents are dissolved or suspended in a liquid aqueous vehicle. Although useful, wet chemistry or solution assay techniques typically require analyzer equipment having intricate solution handling and transport capabilities. Analytical equipment of this "wet chemistry" variety is often expensive and complex in terms of liquid handling requirements. An early example of such wet chemistry analyzer equipment is set forth in U.S. Pat. No. 2,797,149.

More recently, various attempts have been made to reduce large scale solution handling and transport problems associated with analytical equipment of the "wet chemistry" variety. For example, as illustrated in Forestiere U.S. Pat. No. 3,036,894 issued May 29, 1962; Johnson et. al. U.S. Pat. No. 3,476,515 issued Nov. 4, 1969; Gulgan, U.S. Pat. No. 3,620,678 issued Nov. 16, 1971; Halbartschlager et. al., U.S. Pat. No. 3,700,089 issued Oct. 24, 1972; Shapiro, U.S. Pat. No. 3,713,780 issued Jan. 30, 1973; Schmidz, U.S. Pat. No. 3,713,775 issued Jan. 30, 1973, and Sirago et. al., U.S. Pat. No. 3,713,779 issued Jan. 30, 1973; there are depicted various analytical clinical elements for the analysis of biological liquids wherein "wet chemistry" clinical analyses are carried out on biological liquid samples by the use of small quantities of liquid reagents which can be prepackaged, carried, and transported in a preformed element composed of individual compartments for the transport and storage of liquid samples and liquid reagents. Many of these clinical analytical elements are manufactured from resilient materials, and the various individual compartments thereof are interconnected with one another such that liquid reagents and liquid biological samples may be transported from one compartment to another by applying external pressure to the analytical element thereby forcing liquid reagent or liquid sample to flow from one compartment through a preformed channel to another compartment or reaction zone.

As a further modification of the above-noted "wet chemistry" analytical techniques, various analytical elements for clinical analysis have been proposed wherein the reagent chemicals required in the assay of a particular biological liquid sample are incorporated in dry form, e.g., tablet form, into a preformed, disposable test element and subsequently transported to other areas of the test element wherein the dry reagent tablet is admixed with the biological liquid sample and the particular assay is then carried out as a conventional solution or "wet chemistry" assay technique. Representative such analytical elements used in the abovedescribed modified "wet chemistry" clinical assay techniques are set forth, for example, in certain embodiments of Johnson et. al., U.S. Pat. No. 3,476,515 issued Nov. 4, 1969; certain embodiments of Adams, U.S. Pat. No. 3,879,263 issued Apr. 22, 1975; certain preferred embodiments of Blackburn et. al., U.S. Pat. No. 3,497,320 issued Feb. 24, 1970; and certain preferred embodiments of Bednar, U.S. Pat. No. 3,504,376 issued Mar. 31, 1970.

As an alternative to wet chemistry and modified wet chemistry or solution assay techniques such as described hereinabove, various analytical elements for clinical analysis have been proposed using "dry chemistry", i.e., analytical techniques wherein chemical reagents in essentially dry form are incorporated in various substantially "dry-to-the-touch" elements such as monolayer test strips, multilayer analytical test elements, and the like. These dry chemistry analytical elements provide for the essentially dry analysis of an analyte and can offer substantial storage, handling and other conveniences compared to wet chemistry and modified wet chemistry analytical techniques. Exemplary analytical elements of the dry chemistry variety are described, for example, in Natelson, U.S. Pat. No. 3,036,893 issued May 29, 1962; Adams et. al., U.S. Pat. No. 3,092,465 issued June 4, 1963, Natelson, U.S. Pat. No. 3,368,872 issued Feb. 13, 1968; Findl, U.S. Pat. No. 3,526,480 issued Sept. 1, 1970; Liotta, U.S. Pat. No. 3,723,064 issued Mar. 27, 1973; Lang et. al., U.S. Pat. No. 3,802,842 issued Apr. 9, 1974; Milligan et. al. U.S. Pat. No. 3,917,453 issued Nov. 4, 1975; Milligan et. al. U.S. Pat. No. 3,933,594 issued Jan. 20, 1976; Przybylowicz et. al., U.S. Pat. No. 3,992,158 issued Nov. 16, 1976; and Verbeck, U.S. Pat. No. 3,993,451 issued Nov. 23, 1976.

The above-noted "dye chemistry" analytical elements offer substantial convenience and handling ease in comparison to many of the above-described "wet chemistry" elements and analytical techniques. Certain of these "dry chemistry" analytical elements, such as those disclosed in the aforementioned Przybylowicz et. al. patent, have been found particularly useful because of their ability to provide quantitative results and their ready adaptability to automated analytical techniques. However, such "dry chemistry" analytical elements, in general, suffer from the disadvantage of being unable to readily accommodate various liquid reagents which may be desirable to necessary in the assay of certain biological liquids. For example, the clinical analysis of certain analytes of serum can often be best conducted under highly alkaline or highly acidic pH conditions. In such cases, of course, it is desirable to conduct the clinical analysis for such analyte in a highly alkaline or highly acidic liquid medium. However, because of the highly corrosive nature of such alkaline and acidic liquids, it is quite difficult and often dangerous to have such corrosive liquids readily available in an analytical laboratory for use by laboratory personnel who are often not highly trained in the proper handling of such chemicals.

In still other clinical assays of biological liquids, it is often desirable to conduct the assay for a given analyte of a biological liquid using a multi-stage reaction sequence wherein the analyte to be processed is subject to first one chemical reagent and then is sequentially subjected (or a reaction product of the first reaction is sequentially subjected) to a second reaction employing a second reagent. In such a sequential reaction, it is often desirable to introduce one reagent at a time subsequent to the initial reaction of the analyte of the liquid sample so that the various reactions required in conducting the assay do not interfere with one another.

As will be apparent, it is quite difficult to physically incorporate, store, or keep a corrosive liquid material which may be needed in a particular assay within conventional dry chemistry analytical test elements such as those illustrated in the aforementioned patents. Similarly, it is often difficult in such dry chemistry analytical elements to perform assays which require sequential reactions, rather than single or simultaneous reactions, to produce a detectable analytical result. Thus, as will be appreciated, it would be particularly desirable to have available an analytical element providing many or most of the advantages associated with dry chemistry analytical elements, but which at the same time would permit one to introduce, without special operator or other special laboratory procedures, corrosive liquids such as high or low pH fluids and/or which would permit one to readily carry out sequential reactions in the assay of a particular analyte without risk of interference between individual reactions.

SUMMARY OF THE INVENTION

In accord with the present invention there is provided an analytical element having the capability of overcoming the foregoing deficiencies. For example, the element of the invention enables one to carry out a clinical assay of an analyte contained in a biological liquid sample using sequential reactions without the risk of potential interference between individual reaction steps, while at the same time providing many, if not all, of the above-noted advantages and convenience associated with "dry chemistry" analytical clinical elements.

In accord with the various embodiments of the analytical element of the present invention, the foregoing advantages are obtained due to the specific structure of the element whereby both dry and liquid reagents can readily be incorporated in the element for use in the assay of the selected analyte. The analytical elements of the invention have a structure comprising a porous layer bearing a substantially planar sample receiving surface; at least one dry reagent material for use in the assay; and one or more associated rupturable pod-like member(s) containing a liquid reagent for the assay, the liquid reagent, upon rupture of such member(s), being released into the element.

As described in detail hereinafter, elements of the invention may embody various structural configurations. For example, analytical elements of the invention may have a structure comprising (a) a porous layer bearing a substantially planar surface to receive from an external source a sample of the biological liquid sample to be assayed, (b) at least one dry reagent material for use in the assay to be performed in the element, such dry reagent material being incorporated in the aforementioned porous layer or in a separate reagent layer, (c) at least one reaction zone comprising a portion of the aforementioned porous layer, or the aforementioned reagent layer, or a separate layer of the element, at least one analytical reaction carried out in the assay to be performed in the element being carried out in this reaction zone, and (d) an associated rupturable pod-like member containing a liquid reagent for the assay to be performed in the element, such liquid reagent, upon rupture of the pod-like member, being released into the aforementioned reaction zone of the element.

The structure of the analytical elements of the present invention is arranged such that each of the abovenoted porous layer, reagent layer, and reaction zone are in fluid contact with one another under conditions of use of the element. Such fluid contact has reference to the ability of a liquid sample to pass between superposed layers or zones of an analytical element. Stated in another manner, fluid contact refers to the ability of components of a liquid to pass between the layers or zones in fluid contact. Although layers or zones in fluid contact can be contiguous, they may also be separated by intervening layers or zones. However, layers or zones in the element that physically intervene layers identified as being in fluid contact will also be in fluid contact and will not prevent the passage of fluid between such layers or zones.

DESCRIPTION OF THE PREFERRED EMBODIMENTS

Figure 1:
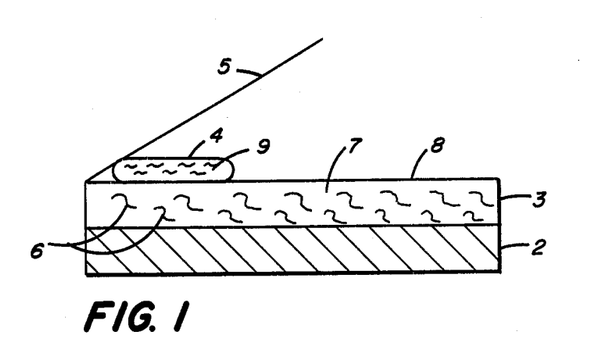
FIG. 1-6 diagrammatically illustrate various embodiments of analytical elements within the scope of the present invention as set forth in further detail hereinafter.

As will be appreciated the element of the invention can be embodied in a variety of different structures. One embodiment of an element of the present invention is illustrated in FIG. 1 attached hereto. In the embodiment of FIG. 1 there is illustrated an element having a porous layer 3 optionally carried on a support 2. Dry reagent material 6 is incorporated in porous layer 3 and represents a material interactive with the particular analyte to be assayed. The element illustrated in FIG. 1 also has present a substantially planar sample receiving surface 8 and associated rupturable pod-like member 4. Located in the interior of pod-like member 4 is liquid reagent 9 for use in the assay to be carried out in the element. In the embodiment shown in FIG. 1 there is also present an optional cover sheet 5 which can be temporarily or permanently hinged to one or more edges of the element.

In operation, a biological liquid sample is applied to sample receiving surface 8 of the element illustrated in FIG. 1 thereby permitting the liquid sample to penetrate into porous layer 3 which is permeable to at least certain components of the biological liquid sample. In the interior of porous layer 3 the components of the liquid sample to which porous layer 3 is permeable interact with dry reagent material 6. Depending upon the particular assay procedure to be carried out by the use of the element shown in FIG. 1, liquid reagent contained in rupturable pod-like member 4 can be introduced into the interior of porous layer 3 substantially simultaneously with the application of the biological liquid sample to sample receiving surface 8; or one can use the element shown in FIG. 1 to carry out an assay which employs a sequential reaction mechanism. For example, the liquid sample applied to surface 8 of porous layer 3 can be allowed to migrate into porous layer 3 to interact with dry reagent material 6 and thereafter pod-like member 4 can be ruptured to release liquid reagent 9 to sequentially interact with the reaction products of the initial reaction between dry reagent material 6 and the liquid sample initially applied to surface 8. In either case, it will be appreciated that in the element of FIG. 1 the interior of porous layer 3 represents the reaction zone 7 for the interaction of liquid reagent 9 in the analytical assay carried out in the element. In a typical case wherein the biological liquid sample applied to receiving surface 8 of the element of FIG. 1 is analyte positive, a detectable change, e.g., a color change, occurs in porous layer 3 as a result of the interaction of liquid reagent material 9 and dry reagent material 6 with one or more components (or reaction products thereof) of the liquid sample.

In the case where the element of FIG. 1 has a support present, the support can be a radiation-transmissive material, i.e., at least wholly or partially transparent or translucent to radiation having a wavelength corresponding to any radiation-detectable change in layer 3, so that in the case of an analyte positive liquid sample, one can detect the radiational change in porous layer 3 through support 2. In the case where support 2 is opaque, one can detect any radiational change occurring in porous layer 3 directly from the top surface of porous layer 3. Of course, in the case where support 2 is absent, for example, in the situation where porous layer 3 represents a self-supporting porous material, such as filter paper, a porous synthetic polymer material, e.g., a coated polymer film or a synthetic woven fabric, one can detect the radiational change occurring in porous layer 3 directly from either the top or bottom surface thereof.

In the case where the element illustrated in FIG. 1 has present optional cover sheet 5, it will be appreciated that this cover sheet can perform a variety of useful functions. For example, upon application of the biological liquid sample to surface 8 of the element, cover sheet 5 can be closed to form an essentially liquid tight seal between sample receiving surface 8 and the interior surface of cover sheet 5. In such case, one can then effect rupture of pod-like member 4 and the release of liquid reagent 9 from member 4 into reaction zone 7 without obtaining any undesireable leakage of liquid reagent 9 to the outside of the element. This represents a particularly desireable feature especially where liquid reagent 9 represents a material, for instance, a highly corrosive material such as a very high or very low pH liquid, which would otherwise present difficult liquid handling problems. In such case, the liquid tight seal formed by the closure of cover sheet 5 and porous layer 3 can be either permanent or temporary. For example, if liquid reagent material 9 is a high or a low pH aqueous liquid which is essentially deactivated upon neutralization and evaporation of the aqueous components thereof, one can remove cover sheet 5 upon deactivation of liquid reagent 9 and retain the remainder of the element bearing the record of the detectable change occurring in layer 3 (which is related to the presence or concentration of the analyte being assayed).

Figure 2:
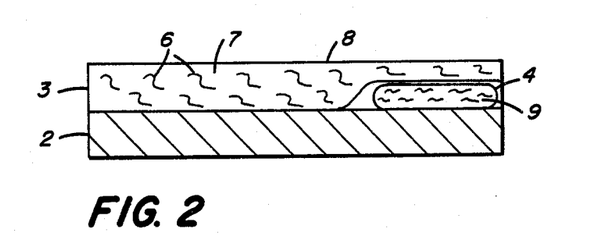

A further embodiment of an element exhibiting the structure characteristic of the present invention is set forth in FIG. 2. In the element of FIG. 2 the various features thereof designated by numerals 2–9 refer to the same features indicated by numerals 2–9 in FIG. 1 described hereinabove. It will be noted that the element of FIG. 2 differs from that of FIG. 1 in that rupturable pod-like member 4, rather than being associated with the planar sample receiving surface 8 of the element, is physically incorporated entirely within the element of FIG. 2 and associated with the bottom surface of porous layer 3. In this manner, one can completely retain liquid reagent 9 within the interior of the element of FIG. 2 without the use of a separate cover sheet 5 such as illustrated in FIG. 1, and/or one is also afforded the opportunity of introducing liquid reagent 9 into reaction zone 7 from a direction and location which is different from that of the initial liquid sample introduced into the element at sample receiving surface 8.

If desired, porous layer 3 can be temporarily adhered to support 2 such that upon completion of the assay in the element of FIG. 2 and any desireable or necessary deactivation of liquid reagent material 9, one can strip layer 3 from support 2. If pod-like member 4 is permanently attached to support 2, upon stripping layer 3 from support 2, one can discard both support 2 and ruptured member 4 and retain only member 3, if desired, for record purposes. To enhance stripping of layer 3 from support 2, an optional porous stripping layer (not shown) can be present between layers 3 and 2 of FIG. 2.

Figure 3:
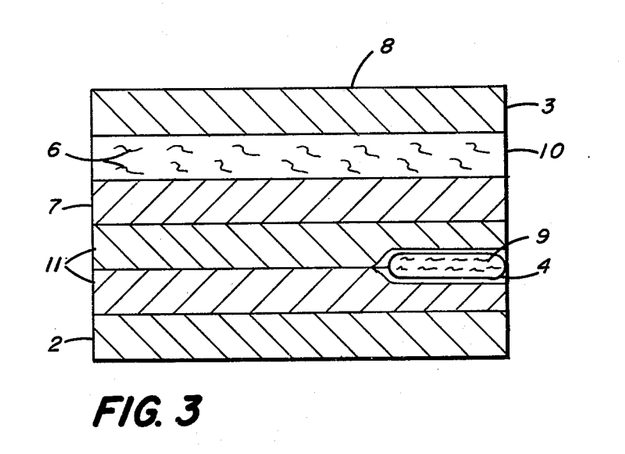

In FIG. 3 attached hereto there is illustrated yet another embodiment of the invention. In this multilayer element substantially planar sample receiving layer 8 represents the surface of porous layer 3, such porous layer in the element of FIG. 3 being more specifically identified as a spreading layer which has isotropic porosity and substantially uniform permeability to the applied biological liquid sample. Such liquid sample spreading layers have been found particularly useful because of their unique ability to absorb and spread applied liquid sample so that as the liquid sample permeates through the layer, the spreading layer produces a uniform apparent concentration of spread substances per unit area at its surface facing an underlying adjacent layer of the element. Such spreading layers are described in further detail in Przybylowicz and Millikan, U.S. Pat. No. 3,992,158 issued Nov. 16, 1976. Underlying spreading layer 3 in the element of FIG. 3 is reagent layer 10 containing a dry reagent material 6 which physically or chemically takes part in the reaction scheme of the particular assay being carried out in the element. Typically, although not required, reagent layer 10 also contains a porous matrix material in which dry reagent 6 can be incorporated. Typically, the matrix of the reagent layer represents a material inert with respect to the reactions being carried out in the assay and serves merely as a medium which is permeable to at least those components of the liquid sample taking part in the reaction procedure employed in the assay and/or provides a physical carrier for dry reagent material 6.

Desireably, although not required, reagent layer 10, like layer 3, can be of uniform permeability to at least those components of the applied liquid sample being assayed or to reaction products formed between components of the applied liquid sample and reagent material 6 contained in reagent layer 10. Of course, in certain cases factors such as uniform permeability of various layers, such as reagent layer 10 and porous layer 3, may be undesirable or unnecessary so that these layers either should not or need not have uniform permeability characteristics. As further illustrated in the element of FIG. 3, rupturable pod-like member 4 is present underlying reagent layer 10 such that upon rupture of member 4 liquid reagent material 9 is released into reaction zone 7. As shown in FIG. 3, optional porous layer(s) 11 may also be present in the element to absorb excess liquid reagent material 9 or to form an extension of reaction zone 7. Also illustrated in FIG. 3 is the presence of optional support 2 which may be present where necessary or desireable, such as in situations where none of the aforementioned layers or zones, such as 3, 7, 10, or optional layer(s) 11 are self-supporting, either by themselves or in combination.

Figure 4:
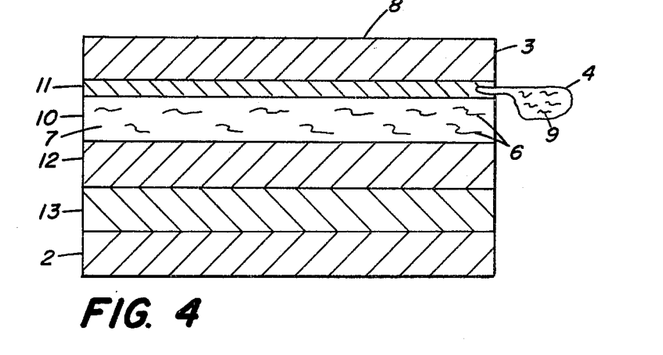

A further embodiment of the element of the present invention is illustrated in FIG. 4. It will be recognized that the element in FIG. 4 is identical to that illustrated in FIG. 5 of Figueras, copending U.S. Patent Application Ser. No. 759,527 filed Jan. 14, 1977. This element of the present invention is illustrated in FIG. 5 of the aforementioned Figueras U.S. Patent Application because it has a structure which makes this element particularly suitable for use in certain aspects of the invention described in that patent application. In the element illustrated in attached FIG. 4, porous layer 3 bearing substantially planar sample receiving surface 8 represents an isotropically porous spreading layer. Underlying layer 3 is rupturable pod-like member 4 containing liquid reagent material 9. Pod-like member 4 is sandwiched between or within individual porous spacer layer 11. In the element shown in FIG. 4 reagent layer 10 underlies member 4 and contains dry reagent material 6. Layer 12 in the element of FIG. 4 represents a radiation blocking layer which is composed of an opacifying agent such as a particulate pigment material or a blush polymer material. Layer 12 is permeable to at least one or more components of the biological liquid sample applied to layer 8 or to a reaction product thereof so that these components are able to pass through layer 12 to registration layer 13 which serves as a receiving layer for such components. Typically, the components passing through layer 12 contain a preformed detectable group which has been released from layer 10 or a precursor for a detectable species, such as a dye precursor which can form a colored or otherwise detectable species upon interaction with an additional reagent material incorporated in layer 13. As a result, the colored or otherwise detectable products which are present in layer 13 may be detected therein, for example, by reflection spectrophotometry carried out by passing a light beam of appropriate wavelength through support layer 2 which can be transmissive to radiation of such wavelength. As a result, the light beam is reflected from radiation blocking layer 12 and the absorption characteristics of the reflected light beam can be used to evaluate the presence or concentration of the detectable material formed in layer 13. In the element of FIG. 4, reaction zone 7 into which liquid reagent material 9 is released is present in reagent layer 10. Of course, it will be appreciated that by selecting appropriate porous matrix materials for the composition of reagent layer 10 or porous layers 3 and 11, these layers can be constituted such that only one or all of these layers is permeable to liquid reagent material 9. Thus, although reaction zone 7 is shown as a portion of reagent layer 10 in FIG. 4, depending upon the individual permeability characteristics of layer 10 and layers 3 and 11 to liquid reagent material 9, reaction zone 7 can also extend into a portion of layer 3 or layer 11 or it can be confined exclusively to layer 3, layer 11, or layer 10. For example, in certain assay procedures it may be desired to effect interaction between liquid reagent material 9 and certain components of the applied liquid sample before the sample contacts dry reagent material 6 contained in reagent layer 10 of the element shown in FIG. 4. In this case, the composition of the matrix material of reagent layer 10 be selected such that it is selectively permeable, i.e., capable of substantially blocking the passage of any amount of liquid reagent material 9 while permitting the passage of certain components of the liquid sample applied to surface 8 or to at least certain reaction products formed between these components and liquid reagent material 9.

Figure 5:
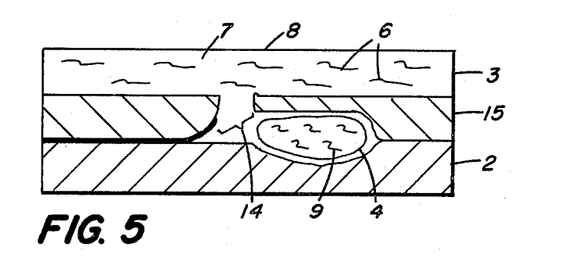
Figure 6:
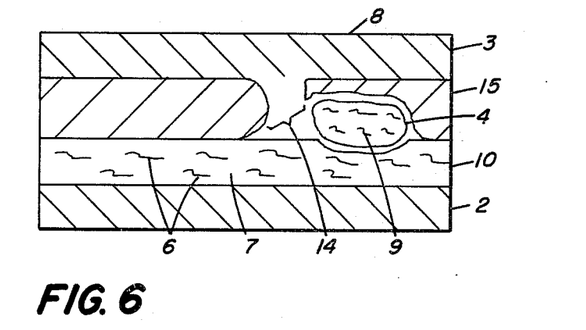

FIGS. 5 and 6 represent still further embodiments of the elements of the invention. In these elements, those features thereof labelled 2–9 are identical to items labelled 2–9 of FIGS. 1–4. However, in the elements of FIGS. 5 and 6, additional layer 15 containing opening(s) 14 has been incorporated therein. The function of opening 14 is to provide a path or channel through layer 15 thereby facilitating and directing the passage of the liquid reagent material 9 and/or the biological liquid sample into intimate contact with one another in reaction zone 7. Because layer 15 contains individual openings for fluid passage, layer 15 may itself be constructed of a material impermeable to the liquid sample and liquid reagent material.

The dry reagent material which is distributed within the porous layer, reagent layer, reaction zone, or other areas within the analytical elements of the present invention represents a composition that contains one or more components which can interact with the desired analyte or a precursor or reaction product of such analyte contained in the biological liquid sample applied to the element. Such interaction is meant to refer to chemical reactivity, catalytic activity as in the formation of an enzyme-substrate complex, and any other form of chemical or physical interaction that can produce or promote within the analytical element, such as in the reaction zone thereof, a change that is detectable such as by radiometric detection techniques, i.e., by detection techniques which employ measurement of light or other radiation. The dry reagent material can be incorporated within various regions or layers of a particular element of the invention by any of a wide variety of well-known techniques. For example, when the dry reagent material is incorporated into a porous matrix material to constitute a suitable reagent layer or reaction zone of the element, the distribution of dry reagent material within such matrix can be obtained by dissolving or dispersing it in the matrix material. Although uniform distributions of dry reagent material are often preferred within the particular region or layer of an analytical element in which they are to be incorporated, such uniform distributions may not be necessary if the interactive material is, for example, an enzyme. Advantageously, where it is desired to retain a particular dry reagent material(s) used in the invention within a specific layer or zone, the dry reagent may be physically or chemically immobilized within such layer or zone.

As will be apparent, the particular dry reagent materials employed within the element will depend on the analysis of choice. Typical such dry reagent materials include various indicator dye materials and precursors thereof capable of interacting with a particular analyte of choice, enzyme materials, buffering materials, and the like. For example, in carrying out an assay for glucose in a biological fluid such as blood, serum, or urine, the enzyme glucose oxidase may be incorporated as a dry reagent material into a suitable reagent layer of an element of the present invention. Such a dry reagent material may be used in an element for the assay of glucose in combination with a liquid reagent material composed of a mixture of peroxidase and o-toluidine dissolved in a suitable liquid such as an acetone-water solvent, such liquid reagent being contained within the rupturable pod-like member present in the element. In such case the combination of the dry reagent material glucose oxidase together with the liquid reagent material containing peroxidase and o-toluidine are used to form a well-known reagent system for the assay of glucose. As a result of such a reagent system, the presence of glucose in the liquid sample under analysis is revealed by the characteristic appearance of a blue color. Further details concerning such a reagent system for the assay of glucose may be found in various clinical textbooks such as *Clinical Chemistry: Principles And Techniques*, edited by R. J. Henry et al, published by Harper and Row, New York, N.Y., 1968, at page 644.

The liquid reagent material contained in the rupturable pod-like member associated with the elements of the present invention can also be selected from a wide variety of materials which can interact chemically or physically with the analyte of choice or a chemical precursor or reaction product thereof. The liquid reagent material may be dissolved or dispersed in a suitable liquid carrier vehicle or the liquid vehicle itself may be used as the liquid reagent material. In one preferred embodiment, the liquid reagent material comprises a highly corrosive liquid, such as a high or low pH fluid, for use in the particular assay being carried out in the element. In such case, the high or low pH liquid may itself represent the liquid reagent or the high or low pH fluid may contain additional reagent materials dissolved or dispersed therein. The use of a high or low pH fluid is particularly useful, for example, in the case where the dry reagent material incorporated within the element of the invention contains or consists of a preformed detectable material, such as a dye, which is immobilized within a reagent layer contained in the element, but which upon interaction with the analyte of choice in the presence of a high pH fluid is released in proportion to the concentration of the analyte and migrates into another layer of the element, such as a registration layer, where it can be detected. An element particularly suitable for assays which employ the aforementioned dry and liquid reagent materials is set forth in FIG. 4 described hereinabove. For further information regarding specific dye release materials and particular assays employing the same, reference may be made to the above-noted Figueras patent application, U.S. Ser. No. 759,527, filed Jan. 14, 1977.

A further advantage of the element of the present invention is that one may employ therein a dry reagent material and liquid reagent material which are physically or chemically incompatibile with one another if permitted to intermix prior to the particular assay to be carried out. And, of course, anothe advantage of the invention is that by use of the rupturable pod-like member, one may use reagents which are difficult or impossible to employ with a typical dry chemistry analytical element simply because of the fact that they typically can be used only in liquid form.

In addition to the use of a high or low pH liquid, and the use of a liquid form reagent containing a mixture of the enzyme peroxidase and o-toluidine (as described hereinabove with respect to a glucose assay), a variety of other reagents may be incorporated in liquid form within the rupturable pod-like member used in the present invention. For example, in an assay for urea nitrogen contained in a biological liquid such as blood or serum, one can employ an element of the present invention which employs the diacetyldioxime test for urea nitrogen. This is a conventional test for urea nitrogen and reference thereto may be found, for example, in the aforementioned textbook edited by Henry et. al. at page 514. Using such a test for assay of urea nitrogen in an element of the present invention, one can employ an element having the structure illustrated in FIG. 2 hereof. In such case one can construct an element having a support 2 shown in FIG. 2 a transparent polyester film base material over which is positioned a porous layer composed of a glass wool pad suitably affixed to the polyester support, for example, by use of an adhesive along the periphery of the interface between the support and porous layer. Sandwiched between support 2 and porous layer 3 can be pressure rupturable pod-like member 4 suitably adhered along one edge thereof to support 2. The liquid reagent material 9 contained in pod-like member 4 is an iron-thiosemicarbazide-containing liquid composed of 10 milliliters of 2N sulfuric acid in which are dissolved 10 milligrams of ferric chloride and 100 milligrams of thio-semicarbazide. The dry reagent material 6 contained in porous layer 3 consists of the diacetyldioxime reagent which can be incorporated into porous layer 3 by applying an ethanol-water solution thereof to porous layer 3 and subsequently drying the layer to evaporate the ethanol-water solvent vehicle used to apply the diacetyldioxime. Thus, one has an element containing diacetyldioxime as the dry reagent material incorporated in porous layer 3 and an iron-thiosemicarbazide-containing liquid reagent contained in pressure rupturable pod-like member 4. The resultant element, when spotted with a urea nitrogen-containing liquid sample, can be used to assay for the presence and/or concentration of urea nitrogen in the sample through the standard diacetyldioxime test. That is, upon application of the urea nitrogen-containing liquid sample to substantially planar sample receiving surface 8 of porous layer 3 and subsequent to the application of pressure to the element causing the rupture of pod-like member 4 contained therewithin and the release of iron-thiosemicarbazide reagent, the conventional reaction between the urea contained in the liquid sample, the diacetyldioxime and the iron-thiosemicarbazide is obtained to produce a red coloration within porous layer 3, the density or intensity of which is detectable and can be related to the presence and/or concentration of urea nitrogen contained within the biological liquid sample. For purposes of illustration, additional examples of suitable liquid reagent materials are set forth hereinafter in examples 1-4.

The rupturable pod-like member contained in the element of the present invention may be constructed of a variety of materials. Rupture of the member can be effected by diverse means including pressure, solvents, heat, combinations of the foregoing, etc. In accord with a particularly preferred embodiment of the present invention the rupturable pod-like member is a rupturable container similar to those employed in various well-known light sensitive silver halide photographic film units. Rupturable pod containers of this type are disclosed for example in U.S. Pat. Nos. 2,543,181; 2,643,886; 2,653,732; 2,723,051; 3,056,492; 3,056,491 and 3,152,512. In general, such containers are prepared from a rectangular sheet of fluid- and air- impervious material folded longitudinally upon itself to form two walls which are sealed to one another along the longitudinal and end margins to form a cavity in which the liquid reagent material is contained.

Irrespective of the particular construction of the rupturable pod-like member, the member or members which are employed in an element of the present invention can be incorporated into the element by a multiplicity of different techniques depending upon the particular location of the member in the element, the materials used to construct the pod-like member and those used to construct the other portions of the element of the invention, and the like. If more than one pod is used in the element to carry out a particular analytical reaction, these pods may be arranged in series or parallel. Typically, the pod-like members are affixed such as by an adhesive or heat-sealing to one or more self supporting layers contained within the element of the invention. Alternatively, the pod-like member may be constructed such that one end or margin thereof can be mechanically coupled to other layers of the element such as by a staple or other mechanical coupling means.

As mentioned previously, elements of this invention can include a radiation-blocking layer (see the embodiment of the present invention illustrated in FIG. 4), preferably interposed between a reagent layer and the registration layer. Radiation-blocking layers are permeable to the detectable species or a precursor thereof formed in the element and serve to inhibit passage of electromagnetic radiation, such as at the wavelength or wavelengths used for detection. Using such a layer, color or other potential interferents to result detection can be masked from the registration layer or the reagent layer, depending which of these layers is used to monitor the detectable species. Radiation-blocking layers include an opacifying agent that, by virtue of its absorbance, reflectance or the like, provides a radiation inhibiting effect when incorporated into the layer. In one aspect, the radiation-blocking layer can include a matrix containing an opacifying agent, such as a pigment like carbon or other inorganic pigment such as a metal salt like titanium dioxide, zinc oxide, barium sulfate, etc. Blushed polymers, which are generally reflective in nature, can comprise the opacifying agent, and layers of such blushed polymers can be effectively used as radiation-blocking layers. It will be appreciated that if a microporous, blushed polymer layer is used as a radiation-blocking layer, such layer can also serve as a filtering layer. Such a layer is useful, for example, in an element as shown in FIG. 4 in the event that registration layer 13 thereof is permeable to filterable substances which could impair result detection in the registration layer if allowed to enter the registration layer from reagent layer 10.

In one preferred aspect, blushed polymer layers can also incorporate a reflective inorganic pigment, such as the highly reflective pigments mentioned elsewhere herein, to enhance reflectivity and/or spreading (as described hereinafter with respect to spreading layers). The amount of pigment that can be included in a layer together with blushed polymer is highly variable, and amounts of from about 5 percent by weight to about 1,000 percent by weight of pigment based on the weight of blushed polymer are preferred, with a pigment concentration of from about 100 weight percent to about 600 weight percent pigment based on the blushed polymer being most preferred.

As mentioned previously, an element of this invention can optionally include a spreading layer as the porous layer bearing the substantially planar sample receiving surface. Such spreading layers are described, in detail, in Przybylowicz and Millikan, U.S. Pat. No. 3,992,158, issued Nov. 16, 1976. The spreading layer is a layer than can accept a liquid sample, whether applied directly to the spreading layer or provided to it from a layer or layers in fluid contact with the spreading layer, and within which the solvent or dispersion medium of the sample and at least one solute, dispersoid (constituent of the dispersed or internal phase) or reaction product of solute or dispersoid is distributed such that a uniform apparent concentration of such substance, i.e., solute, dispersoid or reaction product thereof (which can be an analyte or an analyte precursor), is provided at the surface of the spreading layer facing any adjacent underlying layer(s) of the element. It will be appreciated that such an apparent concentration can be achieved with concentration gradients present through the thickness of or otherwise in the spreading layer. Such gradients do not present any difficulty to obtaining quantitative test results and can be accommodated using known calibration techniques.

The spreading layer advantageously produces a uniform apparent concentration of spread substance per unit area at its surface facing a reagent layer with which the spreading layer is in fluid contact. Such uniformity of apparent concentration can be determined by densitometric or other analytical techniques, such as is described in U.S. Pat. No. 3,992,158.

Useful spreading or metering layers are desirably isotropically porous layers. Such layers can be prepared using a variety of components. In one aspect, particulate material can be used for form such layers, wherein the isotropic porosity is created by interconnected spaces between the particles. Various types of particulate matter, all desirably chemically inert to sample components under analysis, are useful. Pigments, such as titanium dioxide, barium sulfate, zinc oxide, etc., are desirable. Other desirable particles are diatomaceous earth and microcrystalline colloidal materials, e.g., microcrystalline cellulose, derived from natural or synthetic polymers. Spherical particles of uniform size or sizes, such as resinous or glass beads, can also be used and may be particularly desirable where uniform pores are advantageous, such as for selective filtration purposes. If a particulate material of choice is not adherent, as in the case of glass beads or the like, it can be treated to obtain particles that can adhere to each other at points of contact and thereby facilitate formation of an isotropically porous layer. As an example of suitable treatment, non-adherent particles can be coated with a thin adherent layer, such as a solution of hydrophilic colloid like gelatin or polyvinyl alcohol, and brought into mutual contact in a layer. When the colloid coating dries, the layer integrity is maintained and open spaces remain between its component particles.

As an alternative or in addition to such particulate materials, the spreading layer can be prepared using isotropically porous polymer compositions. It is possible to prepare such polymer compositions using techniques useful in forming blushed polymers, for example, as described in U.S. Pat. No. 3,992,158. Other techniques useful in preparing isotropically porous polymer compositions include those relating to the use of gas or other swellable constituents to create pores, as described in U.S. Pat. Nos. 2,960,728 and 2,946,095; or to the use within the polymer phase of a dissolvable solid that is dissolved to provide pores, for example, as discussed in U.S. Pat. No. 3,816,575.

Many different polymers can be used, singly or in combination, for preparing isotropically porous blushed polymer spreading layers for use in this invention, typical examples being polycarbonates, polyamides, polyurethanes and cellulose esters such as cellulose acetate. Various microporous filters are, or are partly, blushed polymeric compositions, for example, various membrane filters of Millipore Corporation, and they have been described in patents such as U.S. Pat. Nos. 2,783,894 and 2,772,322.

Porous layers and spreading layers useful in the elements described herein can be prepared by coating from solution or dispersion. The range of materials useful for inclusion in any such layer is widely variable as discussed herein. If desired or if necessary, suitable dry reagent materials may be incorporated in the porous and isotropically porous spreading layers described in the elements of the invention. The thickness of these porous layers are variable and will depend in part on the intended sample volume, which for convenience and cleanliness the layer sould be able to absorb, and on the layer's void volume, which also affects the amount of sample that can be absorbed into the layer. Porous layers of from about 50 microns to about 300 microns dry thickness have been particularly useful. However, wider variations in thickness are acceptable and may be desirable for particular elements.

When preparing an isotropically porous spreading layer, it is useful to have void volume comprise at least about 25% of the total layer volume, and void volumes of from 50–95% may be desirable. Variations in void volume of porous layers can be used advantageously to modify element absorbing characteristics. It will be appreciated that the pore size in any case should be sufficient to permit migration of sample components or other substances desirably provided to other layers of the element.

In preparing integral analytical elements of this invention, the layers can be preformed as separate layers which can thereafter be laminated prior to use or maintained as separate layers until brought into fluid contact when the element is in use. Layers preformed as separate members, if coatable, are typically coated from solution or dispersion on a surface from which the layer can be physically stripped when dried. However, a convenient procedure which can avoid problems of multiple stripping and lamination steps when contiguous layers are desired, is to coat an initial layer on a stripping surface or a support, as desired, and thereafter to coat successive layers directly on those coated previously. Such coating can be accomplished by hand, using a blade coating device or by machine, using techniques such as dip or bead coating. If machine coating techniques are used, it is often possible to coat adjacent layers simultaneously, using hopper coating techniques well-known in the preparation of light-sensitive photographic films and papers. If it is essential or desirable that adjacent layers be discrete, and maintenance of layer separation by adjustment of coating formulation specific gravity is not satisfactory, as possibly in the case of porous spreading layers, the appropriate selection of components for each layer, including solvent or dispersion medium, can minimize or eliminate interlayer component migration and solvent effects, thereby promoting the formation of well-defined, discrete layers. Any interlayer adhesion problems can be overcome without harmful effect by means of surface treatments including extremely thin application of subbing materials such as are used in photographic films.

For coatable reagent layers, a coating solution or dispersion including the matrix material, if any, and incorporated reagent materials can be prepared, coated as discussed herein and dried to form a dimensionally stable layer. The thickness of any reagent layer and its degree of permeability are widely variable and depend on actual usage. Dry thicknesses of from about 10 microns to about 100 microns have been convenient, although more widely varying thicknesses may be preferable in certain circumstances. For example, if comparatively large amounts of reagent material, e.g., polymeric materials like enzymes, are required, it may be desirable to use slightly thicker reagent layers. Fibrous reagent layers can be formed by impregnation of a fibrous matrix, in accordance with well-known techniques.

Radiation-blocking layers and registration layers can be prepared using methods and thicknesses as used when preparing coatable reagent layers, but with constituents appropriate for the particular layer. In the case of registration layers, in addition to their permeability and radiation-transmissiveness, they are desirably substantially free from any characteristic that might appear as or contribute to mottle or other noise in the detection of an analytical result produced in an integral element of the invention. For example, any variations in color or in texture within the registration layer, as could occur if fibrous materials, e.g., some papers, are used as a permeable medium, may be disadvantageous due to nonuniform reflectance or transmittance of detecting energy. This is also true regarding layers, e.g., radiation-blocking and reagent layers, of which at least the lower surface would be observable by a detection means examining a radiation-transmissive registration layer. Further, although fibrous materials like filter and other papers are generally permeable overall, some such materials typically can exhibit widely ranging degrees of permeability and may not exhibit uniform permeability, for example, based on structural variations such as fiber dimensions and spacing. As a result, such materials are not preferred in registration layers and other layers of elements of the present invention intended for quantitative analytical work.

As mentioned previously herein, the present analytical elements can be self-supporting or carried on a support. Useful support materials include a variety of polymeric materials such as cellulose acetate, poly(ethylene terephthalate), polycarbonates and polyvinyl compounds such as polystyrenes, etc. A support of choice for any particular element will be compatible with the intended mode of result detection. Preferred supports include radiation-transmissive support materials that transmit electromagnetic radiation of a wavelength or wavelengths within the region between about 200 nm and about 900 nm as well as radiation due to radioactivity. For fluorimetric detection of analytical results through the support, it is desirable for the support to transmit over a somewhat wider band than is necessary for non-fluorescence measurements, or, alternatively, to transmit at the absorption and emission spectra of the fluorescent materials used for detection. It may also be desirable to have a support that transmits one or more narrow wavelength bands and is opaque to adjacent wavelength bands. This could be accomplished, for example, by impregnating or coating the support with one or more colorants having suitable absorption characteristics. When an element includes a support, the reagent layer (if present as a separate layer), the radiation-blocking layer (if present), and the registration layer (if present) will usually be interposed in the element between the support and the porous layer bearing the substantially planar sample receiving surface, which often is the outermost layer in an element.

Analytical elements of the present invention can be adapted for use in carrying out a wide variety of chemical analyses in the field of clinical chemistry. They are well suited for use in clinical testing of body fluids, such as blood, blood serum and urine, because in this work a large number of repetitive tests are frequently conducted and test results are often needed a very short time after the sample is taken.

As can be appreciated, a variety of different elements, depending on the analysis of choice, can be prepared in accordance with the present invention. Elements can be configured in a variety of forms, including elongated tapes of any desired width, sheets or smaller chips. Particular elements can be adapted for one or more tests of a single type or a variety of tests of different types. In such latter event, it can be desirable to coat a common support with one or more strips or channels, each optionally of a different composition to form a composite element suited for conducting a variety of desired tests.

In a typical analytical procedure using the present elements, which could be manual or automated, the element is taken from a supply roll, chip packet or other source and positioned to receive a free drop, contact spot or other form of liquid sample, such as from an appropriate dispenser. After sample application, and typically after the liquid sample has been taken up by the porous layer underlying the substantially planar sample receiving surface, the rupturable pod-like member of the element is ruptured. Thereafter or concurrently therewith, the element can be exposed to any conditioning, such as heating, humidification or the like, that may be desirable to quicken or otherwise facilitate obtaining any test result.

After the analytical result is obtained as a detectable change, it is measured, usually by passing the element through a zone in which suitable apparatus for reflection, transmission or fluorescence spectrophotometry is provided. Such apparatus would serve to direct a beam of energy, such as light, which would then be reflected, such as from a radiation-blocking layer in the element, back to a detecting means or would pass through the element to a detector, in the case of transmission detection. Use of reflection spectrophotometry can be advantageous in some situations as it can effectively avoid interference from residues, such as blood cells, which may have been left on or in the layers of the element. Conventional techniques of fluorescence spectrophotometry can also be employed if the detectable species is a fluorescent material. Detection would be accomplished using energy that excites the fluorescent species and a detector that senses its fluorescent emission. Furthermore, when blood serum is tested or means are provided for eliminating unwanted whole blood residues, transmission techniques can be used to detect and quantify the indicating reaction products by directing a flow of radiant energy, for example, ultraviolet, visible, or infrared radiation at one surface of the element and measuring the output of that energy from the opposing surface of the element. Generally, electromagnetic radiation in the range of from about 200 to about 900 nm has been found useful for such measurements, although any radiation to which the element is permeable and which is capable of quantifying the product produced in the element can be used. Various calibration techniques can be used to provide a control for the analysis. As one example, a sample of analyte standard solution can be applied adjacent to the area where the drop of sample is placed in order to permit the use of differential measurements in the analysis.

As further illustrations of the present invention, the following Examples are provided. These Examples are not exhaustive or limiting as to the scope of the invention, but are presented to provide detailed illustrations of certain specific embodiments of the invention.

EXAMPLE 1

Clinical Element for Creatinine Assay Materials

Pressure-rupturable pods were made of strips of polyethylene by folding the strip and sealing the edges by heat. Each pod contained liquid reagent material consisting of 1/10 cc of 1.0 N NaOH solution with 0.75% by weight hydroxyethyl cellulose added as a thickener. Each pod was approximately 1.6 cm. wide and 2.5 cm. long.

Strips of filter paper were dipped in a saturated aqueous picric acid solution, dried and cut into long strips about 1.6 cm. wide.

Creatinine hydrochloride solutions were prepared in 1.0, 0.5, 0.25, and 0.125% by weight concentrations of creatinine hydrochloride dissolved in distilled water.

Preparation of the Clinical Element

Tapes containing the test ingredients were prepared as follows: The pods, which were affixed by an adhesive on a strip of optically clear, 4 mil thick poly(ethylene terephthalate) film about 1.9 cm. wide at about 3.8 cm. intervals, were covered with a strip of the filter paper containing the picric acid to form a reagent layer containing the picric acid as the dry reagent material. Over this reagent layer, there was placed another covering of microporous filter material to form a porous layer. The microporous filter material had a thickness of about 180 microns, an average pore size of about 1.2 microns, and consisted of cellulose acetate nitrate microporous membrane sold by Millipore Corporation under the trademark Millipore MF filter. Each pod and associated, overlying contiguous area of the picric acid-containing reagent layer was isolated into discrete "compartments" by separating each such "compartment" from the other by two-sided adhesive tape. The resultant multilayer tape element was sealed at the edges to form a "sandwich" with the pods inside and consisted essentially of a series of independent analytical assay elements.

EXAMPLE 4

Clinical Element for Uric Acid Assay Materials

Phosphotungstic acid reagent was prepared by refluxing a solution of 4 g sodium tungstate in 30 ml of $H_2O$ with 3.2 ml of 85% by weight orthophosphoric acid for 2 hours. The solution was then cooled to room temperature and diluted to 100 cc. Then 3.2 g of $Li_2SO_4 \cdot H_2O$ was added and mixed well. This liquid reagent material was incorporated into pods prepared as described in Example 1.

An aqueous dope of Na Cerl containing 11% by weight solids was used to dissolve sodium carbonate and prepare a coating on a 4 mil thick sheet of optically clear polyester film. The coating dope contained 20% carbonate (w/v). The coating was yellow and opaque after drying and formed a reagent layer containing dry reagent material. It was cut into long strips about 1.9 cm. wide.

Uric acid stock standard was prepared by dissolving 100 mg of uric acid and 60 mg. of $Li_2CO_3$ at 60° C in 50 ml of $H_2O$, cooled at room temperature and diluted to 100 cc (0.1, 0.05, 0.01% dilutions were made).

Preparation of Clinical Element

A multilayer tape was prepared in a manner somewhat similar to that of Example 3. The pods were adhered to the reagent layer coated polyester film. Next, a strip of polyester film (also 4 mil thick and 1.9 cm. wide) with holes punched in it was placed on top of the pods followed by a top porous spreading layer consisting of a strip of microporous filter material composed of a Millipore Corp. membrane of the type described in Example 1. Double-sized adhesive tape was used to adhere the polyester film with punched holes and the porous spreading layer to underlying layers of the clinical element, the tape being located in the element so that each pod and associated portions of (i) the coated reagent layer, (ii) the overlying area of the punched hole-containing polyester film, and (iii) the overlying area of the porous spreading layer were effectively isolated into individual zones or compartments.

Experimental

A measured drop (10 μl) of a solution of uric acid was placed on the spreading layer side of the test strip directly over a hole in the polyester film below. After the drop had soaked in, the pod was broken and its contents spread between the layers giving a blue color in the reagent layer where the uric acid solution had been absorbed. After two minutes, the density of the blue color from the polyester support side of the element was measured on a reflection spectrophotometer. A concentration series of 0.1%, 0.05%, and 0.01% uric acid solution was run as above and a positive correlation was observed with the produced color density as shown in Table IV.

TABLE IV

| % Uric Acid | Reflection Density of Reagent Layer at 700 nm |
| --- | --- |
| 0.01 | 0.100 |
| 0.05 | 0.148 |
| 0.10 | 0.205 |

The invention has been described in detail with particular reference to certain preferred embodiments thereof, but it will be understood that variations and modifications can be effected within the spirit and scope of the invention.

We claim:

1. An analytical element for the assay of an aqueous liquid sample, said element comprising
    (a) a porous layer structure in which said assay is carried out, said structure being one or more layer compositions selected from the group consisting of porous paper or fabric compostions, permeable polymer film compositions, particle-containing compositions having interconnected open spaces between said particles, and mixtures of the foregoing compositions; said porous layer structure comprising
        (i) a porous layer bearing a substantially planar sample receiving surface to receive said liquid sample from an external source, said porous layer having a layer composition selected from the group defined in (a) hereinabove.
        (ii) at least one dry reagent material for use in said assay, said reagent material being contained in said porous layer or in a separate porous reagent layer having a layer composition selected from the group set forth in (a) hereinabove, and
        (iii) at least one reaction zone comprising a portion of said porous layer, or said porous reagent layer, or a separate porous layer having a composition selected from the group set forth in (a) hereinabove, at least one reaction employed in said assay being carried out in said reaction zone, each of said porous layer, said porous reagent layer, and said reaction zone being in fluid contact with one another; and
    (b) a rupturable pod-like member containing a liquid reagent for said assay, said member being associated with said reaction zone whereby said liquid reagent, upon rupture of said member, is released into said reaction zone.

2. An analytical element as described in claim 1 wherein said element contains a support bearing said porous layer structure.

3. An analytical element as described in claim 1 wherein said element contains a support bearing said porous layer structure and wherein said rupturable pod-like member is sandwiched in a region of said element between said porous layer structure and said support.

4. An analytical element as defined in claim 1 wherein said porous layer (i) is an isotropically porous spreading layer.

5. An analytical element as defined in claim 1 wherein said rupturable pod-like member is pressure-rupturable and is sealed within said element so that upon rupture of said member liquid reagent is contained within said element.

6. An analytical element as defined in claim 1, said element having a cover sheet overlying said substantially planar sample receiving surface.

7. An analytical element as defined in claim 1, said element having a removable cover sheet overlying said substantially planar sample receiving surface.

8. An analytical element as defined in claim 1 wherein said porous layer structure comprises at least two porous layers having a layer composition selected from the group defined in (a), and wherein said element comprises at least one intervening layer between two of said porous layers, said intervening layer comprising a material impermeable to said liquid sample and said liquid reagent, said intervening layer containing at least one

Assay

A measured drop (10 μl) of the creatinine hydrochloride solution was placed on the substantially planar liquid sample receiving surface of the porous layer of the above-described clinical element overlying one of the pods thereof and permitted to soak into the reagent layer. The clinical element was pressed under a roller in the direction of the test drop. This broke the pod and its content was released into the reagent layer containing the absorbed test drop. A reddish-orange color developed in the reagent layer where the creatinine hydrochloride had been absorbed. A concentration series (1.0, 0.5, 0.25 and 0.125% creatinine hydrochloride) was run, and the respective densities of the color produced in the reagent layer were read on a reflection Cary spectrophotometer. A positive correlation between percentage of creatinine and color was found as shown in Table I.

TABLE I

| % Creatinine Hydrochloride | Reflection Density of Reagent Layer at 490 nm |
| --- | --- |
| 0.125 | 1.6 |
| 0.25 | 2.05 |
| 0.5 | 3.0 |
| 1.0 | 3.3 |

EXAMPLE 2

Clinical Element for Alkaline Phosphatase Assay Materials

Pods as described in Example 1 were made containing liquid reagent material consisting of 0.75 cc of an aqueous solution of 2.5% by weight piperazine (hydrate) with 0.75% by weight hydroxyethyl cellulose as a thickener and whose pH had been adjusted to 10.2 with HCl.

A coating was applied to an optically clear, 1.9 cm. wide, 4 mil thick poly(ethylene terephthalate) film from a solution containing 30 mg p-nitrophenyl phosphate disodium salt, 1.5 cc glycine buffer (pH 7) in 15 cc of 10% poly(vinyl alcohol). The coating was dried to form a reagent layer containing a dry reagent material.

Alkaline phosphatase solutions were prepared in 1.0, 0.5, and 0.25% concentrations.

Preparation of Clinical Element

The above-described pods were placed on a strip of the coated reagent layer-containining film and affixed thereto with an adhesive. The pods were spaced on the film as in Example 1. The pods were then covered by a porous layer like that described in Example 1. Two-sided adhesive tape was used to separate each pod from the other to form individual "compartment" in the element. The edges of the resultant multilayer assemblage were sealed with an adhesive to form a multilayer test strip.

Assay

A measured drop (10 μl) of a solution of alkaline phosphatase was placed on the substantially planar sample receiving surface of the porous layer of the test strip and permitted to soak into the underlying reagent layer. The test strip was subjected to roller pressure to rupture the pod and release its contents into the reagent layer coating. A yellowish green color developed at the alkaline phosphatase spot absorbed into the reagent layer. A concentration series of 1, 0.5, and 0.25% alkaline phosphatase solution was tested giving a positive correlation with the density of the color generated when read on a reflection spectrophotometer one minute after breaking the pod. See Table II.

TABLE II

| % Alkaline Phosphatase | Reflection Density of Reagent Layer at 400 nm |
| --- | --- |
| 0.25 | 0.45 |
| 0.50 | 0.90 |
| 1.00 | 1.13 |

EXAMPLE 3

Clinical Element for Total Protein Assay Materials

Pods as described in Example 1 were made containing liquid reagent material consisting of 0.75 cc of 1.0 N NaOH, 4.5% by weight sodium potassium tartrate, 0.5% by weight potassium iodide and 0.6% by weight hydroxyethyl cellulose.

Strips of Whatman ® filter paper No. 4 were dipped in a solution of copper sulfate (5.0 g. in 25 cc of water), dried, and cut into long strips about 1.6 cm. inch wide.

Albumin solutions of 2.5, 5.0 and 7.5% were prepared.

Preparation of Clinical Element

The above-described pods were adhered to a 4 mil thick, optically clear poly(ethylene terephthalate) film about 1.9 cm. wide and covered with another 4 mil thick poly(ethylene terephthalate) film with round holes, about 0.62 cm. in diameter and 3.8 cm. apart, punched in it to permit the layers above to receive the pod solution upon rupture thereof. These punched holes were isolated between adjacent pods by double-sided adhesive tape. Next, the dried filter paper strip impregnated with copper sulfate was placed over the strip containing the punched holes to form a porous layer containing copper sulfate as dry reagent material. Areas of this porous layer overlying the punched holes in the underlying polyester layer were separated from one another by double-sided adhesive tape. All three layers of the resultant multilayer assemblage were sealed at the edges.

Experimental

A drop of the albumin solution (10 μl) was placed on the substantially planar sample receiving surface of the porous layer at the precise spot above the hole punched in the polyester layer below and permitted to soak in. The pod was then broken with a roller and its contents spread over the polyester film base, up through the hole and into the porous layer forming a purple color at the location of the albumin. The density of the colors was measured on a reflection spectrophotometer 1 minute after breaking the pod for a concentration series of 2.5%, 5.0%, and 7.5%. Albumin gave a positive correlation with color density. See Table III.

TABLE III

| % Albumin | Reflection Density of Porous Layer at 560 nm |
| --- | --- |
| 2.5 | 0.42 |
| 5.0 | 0.48 |
| 7.5 | 0.57 | opening to permit fluid contact among layers of said porous layer structure.

9. An analytical element as defined in claim 1 wherein said porous layer structure comprises at least two porous layers having a layer composition selected from the group defined in (a), and wherein said rupturable pod-like member is sandwiched between two of said porous layers, thereby facilitating absorption of liquid reagent released within said element.

10. A method for the assay of an aqueous liquid sample comprising:
 (1) applying said liquid sample to an analytical element comprising a dry reagent material and a liquid reagent, both of which interact in said assay to produce a detectable change in said element corresponding to the presence of analyte, said element comprising
   (a) a porous layer structure in which said assay is carried out, said structure being one or more layer compositions selected from the group consisting of porous paper or fabric compositions, permeable polymer film compositions, particle-containing compositions having interconnected open spaces between said particles, and mixtures of the foregoing compositions; said porous layer structure comprising
     (i) a porous layer bearing a substantially planar sample receiving surface to receive said liquid sample from an external source, said porous layer having a layer composition selected from the group defined in (a) hereinabove,
     (ii) at least one dry reagent material for use in said assay, said reagent material being contained in said porous layer or in a separate porous reagent layer having a layer composition selected from the group set forth in (a) hereinabove, and
     (iii) at least one reaction zone comprising a portion of said porous layer, or said porous reagent layer, or a separate porous layer having a composition selected from the group set forth in (a) hereinabove, at least one reaction employed in said assay being carried out in said reaction zone, each of said porous layer, said porous reagent layer, and said reaction zone being in fluid contact with one another; and
   (b) a rupturable pod-like member containing a liquid reagent for said assay, said member being associated with said reaction zone whereby said liquid reagent, upon rupture of said member, is released into said reaction zone;
 (2) rupturing said pod-like member of said element to release said liquid reagent into said reaction zone of said element; and
 (3) detecting said change produced in said element.

* * * * *